United States Patent
Ark et al.

(10) Patent No.: US 11,229,459 B2
(45) Date of Patent: Jan. 25, 2022

(54) POLYAXIAL BONE SCREW WITH INCREASED ANGULATION

(71) Applicant: K2M, Inc., Leesburg, VA (US)

(72) Inventors: Timmon Ark, Falls Church, VA (US); Theo Choi, Arlington, VA (US); Keenan O'Brien, Grimesland, NC (US)

(73) Assignee: K2M, Inc., Leesburg, VA (US)

( * ) Notice: Subject to any disclaimer, the term of this patent is extended or adjusted under 35 U.S.C. 154(b) by 198 days.

(21) Appl. No.: 16/661,230

(22) Filed: Oct. 23, 2019

(65) Prior Publication Data

US 2020/0054366 A1 Feb. 20, 2020

Related U.S. Application Data

(63) Continuation of application No. 15/664,398, filed on Jul. 31, 2017, now Pat. No. 10,610,265.

(51) Int. Cl.
*A61B 17/70* (2006.01)
*A61B 17/86* (2006.01)

(52) U.S. Cl.
CPC ...... *A61B 17/7052* (2013.01); *A61B 17/7032* (2013.01); *A61B 17/8605* (2013.01); *A61B 17/8685* (2013.01)

(58) Field of Classification Search
CPC .................. A61B 17/70; A61B 17/7032–704
See application file for complete search history.

(56) References Cited

U.S. PATENT DOCUMENTS

| | | |
|---|---|---|
| 5,669,911 A | 9/1997 | Errico et al. |
| 5,891,145 A | 4/1999 | Morrison et al. |
| 5,989,254 A | 11/1999 | Katz |
| 6,090,111 A | 7/2000 | Nichols |
| 6,280,442 B1 | 8/2001 | Barker et al. |
| 6,485,491 B1 | 11/2002 | Farris et al. |
| 6,488,681 B2 | 12/2002 | Martin et al. |
| 6,660,004 B2 | 12/2003 | Barker et al. |
| 6,716,214 B1 | 4/2004 | Jackson |
| 6,736,820 B2 | 5/2004 | Biedermann et al. |

(Continued)

FOREIGN PATENT DOCUMENTS

| | | |
|---|---|---|
| WO | 9812977 A1 | 4/1998 |
| WO | 9849960 A1 | 11/1998 |

(Continued)

*Primary Examiner* — Eduardo C Robert
*Assistant Examiner* — Michelle C Eckman
(74) *Attorney, Agent, or Firm* — Lerner, David, Littenberg, Krumholz & Mentlik, LLP (57) ABSTRACT

A polyaxial bone device includes a screw, a screw housing, and a spring. The screw includes a screw head and a shaft that extends from the screw head. The screw housing defines a longitudinal axis and a bore that extends along the longitudinal axis. The screw housing includes a basewall and opposed sidewalls that extend from the basewall. The basewall defines a notch that receives the shaft to increase pivotal movement between the screw and the screw housing relative to the longitudinal axis of the screw housing. The opposed sidewalls define a rod-receiving channel. The screw housing defines a transverse hole in communication with the bore. The spring is supported in the transverse hole and extends therethrough. The spring extends into the bore to frictionally engage the screw head while the screw head is seated in the bore.

18 Claims, 11 Drawing Sheets

(56) References Cited

U.S. PATENT DOCUMENTS

| | | |
|---|---|---|
| 6,858,030 B2 | 2/2005 | Martin et al. |
| 6,869,433 B2 | 3/2005 | Glascott |
| 6,905,500 B2 | 6/2005 | Jeon et al. |
| 7,087,057 B2 | 8/2006 | Konieczynski et al. |
| 7,250,052 B2 | 7/2007 | Landry et al. |
| 7,264,621 B2 | 9/2007 | Coates et al. |
| 7,291,153 B2 | 11/2007 | Glascott |
| 7,322,981 B2 | 1/2008 | Jackson |
| 7,377,923 B2 | 5/2008 | Purcell et al. |
| 7,476,239 B2 | 1/2009 | Jackson |
| 7,491,218 B2 | 2/2009 | Landry et al. |
| 7,563,264 B2 | 7/2009 | Landry et al. |
| 7,572,279 B2 | 8/2009 | Jackson |
| 7,625,394 B2 | 12/2009 | Molz, IV et al. |
| 7,662,175 B2 | 2/2010 | Jackson |
| 7,678,137 B2 | 3/2010 | Butler et al. |
| 7,682,377 B2 | 3/2010 | Konieczynski et al. |
| 7,686,834 B2 | 3/2010 | Saint Martin |
| 7,691,132 B2 | 4/2010 | Landry et al. |
| 7,695,497 B2 | 4/2010 | Cordaro et al. |
| 7,699,872 B2 | 4/2010 | Farris et al. |
| 7,699,876 B2 | 4/2010 | Barry et al. |
| 7,727,261 B2 | 6/2010 | Barker et al. |
| 7,749,258 B2 | 7/2010 | Biedermann et al. |
| 7,776,067 B2 | 8/2010 | Jackson |
| 7,785,354 B2 | 8/2010 | Biedermann et al. |
| 7,867,258 B2 | 1/2011 | Drewry et al. |
| 7,879,075 B2 | 2/2011 | Shluzas |
| 7,901,435 B2 | 3/2011 | Slivka et al. |
| 7,914,558 B2 | 3/2011 | Landry et al. |
| 7,922,748 B2 | 4/2011 | Hoffman |
| 7,927,360 B2 | 4/2011 | Pond, Jr. et al. |
| 7,942,910 B2 | 5/2011 | Doubler et al. |
| 7,942,911 B2 | 5/2011 | Doubler et al. |
| 7,947,065 B2 | 5/2011 | Hammill, Sr. et al. |
| 7,967,849 B2 | 6/2011 | Carson et al. |
| 7,967,850 B2 | 6/2011 | Jackson |
| 8,021,397 B2 | 9/2011 | Farris et al. |
| 8,034,084 B2 | 10/2011 | Landry et al. |
| RE42,932 E | 11/2011 | Martin et al. |
| 8,048,126 B2 | 11/2011 | Altarac et al. |
| 8,048,133 B2 | 11/2011 | Biedermann et al. |
| 8,057,519 B2 | 11/2011 | Justis et al. |
| 8,070,774 B2 | 12/2011 | Winslow et al. |
| 8,075,592 B2 | 12/2011 | Landry et al. |
| 8,075,599 B2 | 12/2011 | Johnson et al. |
| 8,075,603 B2 | 12/2011 | Hammill, Sr. et al. |
| 8,080,036 B2 | 12/2011 | Shim et al. |
| 8,092,494 B2 | 1/2012 | Butler et al. |
| 8,092,502 B2 | 1/2012 | Jackson |
| 8,097,025 B2 | 1/2012 | Hawkes et al. |
| 8,100,916 B2 | 1/2012 | Kumar et al. |
| 8,100,946 B2 | 1/2012 | Strausbaugh et al. |
| 8,133,262 B2 | 3/2012 | Whipple |
| 8,142,481 B2 | 3/2012 | Warnick |
| 8,162,989 B2 | 4/2012 | Khalili |
| 8,167,910 B2 | 5/2012 | Nilsson |
| 8,167,916 B2 | 5/2012 | Saint-Martin |
| 8,197,517 B1 | 6/2012 | Lab et al. |
| 8,236,035 B1 | 8/2012 | Bedor |
| 8,241,333 B2 | 8/2012 | Jackson |
| 8,257,396 B2 | 9/2012 | Jackson |
| 8,257,399 B2 | 9/2012 | Biedermann et al. |
| 8,267,968 B2 | 9/2012 | Remington et al. |
| 8,267,978 B2 | 9/2012 | Lindemann et al. |
| 8,273,112 B2 | 9/2012 | Garamszegi et al. |
| 8,277,490 B2 | 10/2012 | Freeman et al. |
| 8,292,934 B2 | 10/2012 | Justis et al. |
| 8,298,265 B2 | 10/2012 | Purcell et al. |
| 8,298,274 B2 | 10/2012 | Barker, Jr. et al. |
| 8,313,516 B2 | 11/2012 | Konieczynski et al. |
| 8,317,833 B2 | 11/2012 | Lange et al. |
| 8,337,530 B2 | 12/2012 | Hestad et al. |
| 8,353,932 B2 | 1/2013 | Jackson |
| 8,361,129 B2 | 1/2013 | Chao |
| 8,366,753 B2 | 2/2013 | Jackson |
| 8,377,102 B2 | 2/2013 | Jackson |
| 8,382,811 B2 | 2/2013 | Crook et al. |
| 8,403,962 B2 | 3/2013 | Jackson |
| 8,409,256 B2 | 4/2013 | Arnold et al. |
| 8,409,260 B2 | 4/2013 | Biedermann et al. |
| 8,449,577 B2 | 5/2013 | Kloss et al. |
| 8,449,578 B2 | 5/2013 | Keiser et al. |
| 8,465,530 B2 | 6/2013 | Hammill, Sr. et al. |
| 8,475,495 B2 | 7/2013 | Iott et al. |
| 8,475,501 B2 | 7/2013 | Jackson |
| 8,496,685 B2 | 7/2013 | Landry et al. |
| 8,506,600 B2 | 8/2013 | Carbone et al. |
| 8,506,611 B2 | 8/2013 | Biedermann et al. |
| 8,512,380 B2 | 8/2013 | Farris et al. |
| 8,529,604 B2 | 9/2013 | Barker, Jr. et al. |
| 8,540,753 B2 | 9/2013 | Jackson |
| 8,540,754 B2 | 9/2013 | Slivka et al. |
| 8,556,938 B2 | 10/2013 | Jackson et al. |
| 8,568,451 B2 | 10/2013 | Zucherman et al. |
| 8,574,274 B2 | 11/2013 | Courtney et al. |
| 8,579,949 B2 | 11/2013 | Farris |
| 8,636,769 B2 | 1/2014 | Jackson |
| 8,636,775 B2 | 1/2014 | Purcell et al. |
| 8,636,777 B2 | 1/2014 | Jackson |
| 8,636,778 B2 | 1/2014 | Gephart et al. |
| 8,657,858 B2 | 2/2014 | Garamszegi et al. |
| 8,663,288 B2 | 3/2014 | Konieczynski et al. |
| 8,663,290 B2 | 3/2014 | Doubler et al. |
| 8,663,291 B2 | 3/2014 | Doubler et al. |
| 8,679,162 B2 | 3/2014 | Strausbaugh et al. |
| 8,685,064 B2 | 4/2014 | Hestad et al. |
| 8,690,925 B2 | 4/2014 | Biedermann et al. |
| 8,696,711 B2 | 4/2014 | Jackson |
| 8,709,050 B2 | 4/2014 | Shluzas |
| 8,709,051 B2 | 4/2014 | Hammer et al. |
| 8,740,947 B2 | 6/2014 | Rezach |
| 8,764,810 B2 | 7/2014 | Biedermann et al. |
| 8,795,337 B2 | 8/2014 | Wilcox et al. |
| 8,845,695 B2 | 9/2014 | Saint-Martin |
| 8,864,803 B2 | 10/2014 | Biedermann et al. |
| 8,870,927 B2 | 10/2014 | Matthis et al. |
| 8,870,930 B2 | 10/2014 | Carbone et al. |
| 8,894,692 B2 | 11/2014 | Martin et al. |
| 8,906,068 B1 | 12/2014 | Bedor |
| 8,911,484 B2 | 12/2014 | Lei et al. |
| 8,915,945 B2 | 12/2014 | Carson et al. |
| 8,926,671 B2 | 1/2015 | Biedermann et al. |
| 8,936,624 B2 | 1/2015 | Shluzas |
| 8,940,031 B2 | 1/2015 | Courtney et al. |
| 8,945,194 B2 | 2/2015 | Biedermann et al. |
| 8,951,294 B2 | 2/2015 | Gennari et al. |
| 8,956,362 B2 | 2/2015 | Landry et al. |
| 8,961,568 B2 | 2/2015 | McKinley et al. |
| 8,986,349 B1 | 3/2015 | German et al. |
| 8,992,578 B2 | 3/2015 | Slivka et al. |
| 8,998,958 B2 | 4/2015 | Dauster et al. |
| 9,060,814 B2 | 6/2015 | Doubler et al. |
| 9,078,715 B2 | 7/2015 | Biedermann et al. |
| 9,084,634 B1 | 7/2015 | Lab et al. |
| 9,095,379 B2 | 8/2015 | Chao et al. |
| 9,119,673 B2 | 9/2015 | Cawley et al. |
| 9,131,972 B2 | 9/2015 | Kang et al. |
| 9,144,444 B2 | 9/2015 | Jackson |
| 9,149,300 B2 | 10/2015 | Biedermann et al. |
| 9,155,566 B2 | 10/2015 | Johnson et al. |
| 9,155,579 B2 | 10/2015 | Konieczynski et al. |
| 9,168,069 B2 | 10/2015 | Jackson et al. |
| 9,192,417 B2 | 11/2015 | Biedermann et al. |
| 9,216,041 B2 | 12/2015 | Jackson et al. |
| 9,232,969 B2 | 1/2016 | Farris |
| 9,247,965 B2 | 2/2016 | Biedermann et al. |
| 9,259,247 B2 | 2/2016 | Chandanson et al. |
| 9,271,760 B2 | 3/2016 | Biedermann et al. |
| 9,277,938 B2 | 3/2016 | Biedermann et al. |
| 9,277,942 B2 | 3/2016 | Biedermann et al. |
| 9,289,244 B2 | 3/2016 | Hestad et al. |
| 9,308,027 B2 | 4/2016 | Jackson |
| 9,339,304 B2 | 5/2016 | Biedermann et al. |

(56) References Cited

U.S. PATENT DOCUMENTS

| | | | |
|---|---|---|---|
| 9,358,047 | B2 | 6/2016 | Mishra et al. |
| 9,456,853 | B2 | 10/2016 | Jackson |
| 9,504,494 | B2 | 11/2016 | Ramsay et al. |
| 9,597,121 | B2 | 3/2017 | Matthis et al. |
| 9,603,632 | B1* | 3/2017 | Gunn .............. A61B 17/7037 |
| 9,700,355 | B2 | 7/2017 | Longtain et al. |
| 10,610,265 | B1* | 4/2020 | Ark .................. A61B 17/7052 |
| 2005/0096653 | A1 | 5/2005 | Doubler et al. |
| 2005/0261687 | A1 | 11/2005 | Garamszegi et al. |
| 2005/0267472 | A1 | 12/2005 | Biedermann et al. |
| 2006/0084987 | A1 | 4/2006 | Kim |
| 2006/0149235 | A1 | 7/2006 | Jackson |
| 2006/0200131 | A1 | 9/2006 | Chao et al. |
| 2006/0200136 | A1 | 9/2006 | Jackson |
| 2006/0293665 | A1 | 12/2006 | Shluzas |
| 2007/0123870 | A1 | 5/2007 | Jeon et al. |
| 2007/0208344 | A1 | 9/2007 | Young |
| 2007/0233078 | A1 | 10/2007 | Justis et al. |
| 2007/0233086 | A1 | 10/2007 | Harms et al. |
| 2008/0015579 | A1 | 1/2008 | Whipple |
| 2008/0015596 | A1 | 1/2008 | Whipple |
| 2008/0039843 | A1 | 2/2008 | Abdou |
| 2008/0058811 | A1 | 3/2008 | Alleyne et al. |
| 2008/0154315 | A1 | 6/2008 | Jackson |
| 2008/0177321 | A1* | 7/2008 | Drewry .............. A61B 17/7037 |
| | | | 606/266 |
| 2008/0177335 | A1 | 7/2008 | Melkent |
| 2008/0200956 | A1 | 8/2008 | Beckwith et al. |
| 2008/0269809 | A1 | 10/2008 | Garamszegi |
| 2008/0306534 | A1 | 12/2008 | Winslow et al. |
| 2009/0018591 | A1 | 1/2009 | Hawkes et al. |
| 2009/0062866 | A1 | 3/2009 | Jackson |
| 2009/0076552 | A1 | 3/2009 | Tornier |
| 2009/0093844 | A1 | 4/2009 | Jackson |
| 2009/0105769 | A1 | 4/2009 | Rock et al. |
| 2009/0105770 | A1 | 4/2009 | Berrevoets et al. |
| 2009/0254125 | A1 | 10/2009 | Predick |
| 2009/0326582 | A1 | 12/2009 | Songer et al. |
| 2010/0087873 | A1 | 4/2010 | Null et al. |
| 2010/0094349 | A1 | 4/2010 | Hammer et al. |
| 2010/0114180 | A1 | 5/2010 | Rock et al. |
| 2010/0131018 | A1 | 5/2010 | Konieczynski et al. |
| 2010/0137920 | A1 | 6/2010 | Hammill, Sr. et al. |
| 2010/0191293 | A1 | 7/2010 | Jackson |
| 2010/0204738 | A1 | 8/2010 | Kirschman |
| 2010/0234902 | A1 | 9/2010 | Biedermann et al. |
| 2010/0241175 | A1 | 9/2010 | Walker et al. |
| 2010/0262196 | A1 | 10/2010 | Barrus et al. |
| 2010/0292740 | A1 | 11/2010 | Garamszegi et al. |
| 2010/0298891 | A1 | 11/2010 | Jackson |
| 2010/0305621 | A1 | 12/2010 | Wang et al. |
| 2010/0312279 | A1 | 12/2010 | Gephart et al. |
| 2010/0331886 | A1 | 12/2010 | Fanger et al. |
| 2011/0040338 | A1 | 2/2011 | Jackson |
| 2011/0077694 | A1 | 3/2011 | Biedermann et al. |
| 2011/0087288 | A1 | 4/2011 | Stevenson et al. |
| 2011/0098755 | A1 | 4/2011 | Jackson et al. |
| 2011/0106175 | A1 | 5/2011 | Rezach |
| 2011/0106176 | A1 | 5/2011 | Jackson |
| 2011/0112578 | A1 | 5/2011 | Keiser et al. |
| 2011/0125196 | A1 | 5/2011 | Quevedo et al. |
| 2011/0178558 | A1 | 7/2011 | Barry |
| 2011/0184474 | A1 | 7/2011 | Richelsoph |
| 2011/0196431 | A1 | 8/2011 | Chao et al. |
| 2011/0218579 | A1 | 9/2011 | Jackson |
| 2011/0251650 | A1 | 10/2011 | Biedermann et al. |
| 2011/0257690 | A1 | 10/2011 | Rezach |
| 2011/0270321 | A1 | 11/2011 | Prevost et al. |
| 2011/0282399 | A1 | 11/2011 | Jackson |
| 2011/0282402 | A1 | 11/2011 | Chao et al. |
| 2011/0301646 | A1 | 12/2011 | Kretzer et al. |
| 2011/0301650 | A1 | 12/2011 | Johnson et al. |
| 2011/0301651 | A1 | 12/2011 | Kirschman |
| 2011/0319939 | A1 | 12/2011 | Kretzer et al. |
| 2011/0319946 | A1 | 12/2011 | Levy et al. |
| 2012/0010661 | A1 | 1/2012 | Farris et al. |
| 2012/0016425 | A1 | 1/2012 | Shaffrey et al. |
| 2012/0022597 | A1 | 1/2012 | Gephart et al. |
| 2012/0035663 | A1 | 2/2012 | Jackson |
| 2012/0035670 | A1 | 2/2012 | Jackson et al. |
| 2012/0046699 | A1 | 2/2012 | Jones et al. |
| 2012/0046700 | A1 | 2/2012 | Jackson et al. |
| 2012/0059426 | A1 | 3/2012 | Jackson et al. |
| 2012/0089196 | A1 | 4/2012 | Jackson |
| 2012/0109218 | A1 | 5/2012 | Farris |
| 2012/0123486 | A1 | 5/2012 | Werner et al. |
| 2012/0143262 | A1 | 6/2012 | Jensen et al. |
| 2012/0143265 | A1 | 6/2012 | Biedermann et al. |
| 2012/0143266 | A1 | 6/2012 | Jackson et al. |
| 2012/0165881 | A1 | 6/2012 | Biedermann et al. |
| 2012/0197313 | A1 | 8/2012 | Cowan |
| 2012/0197314 | A1 | 8/2012 | Farris |
| 2012/0209335 | A1 | 8/2012 | Termyna et al. |
| 2012/0215263 | A1 | 8/2012 | Lee |
| 2012/0215264 | A1 | 8/2012 | Lee |
| 2012/0232598 | A1* | 9/2012 | Hestad .............. A61B 17/7038 |
| | | | 606/305 |
| 2012/0310284 | A1 | 12/2012 | Gerchow |
| 2013/0013003 | A1 | 1/2013 | Carbone et al. |
| 2013/0046345 | A1 | 2/2013 | Jones et al. |
| 2013/0046350 | A1 | 2/2013 | Jackson et al. |
| 2013/0053889 | A1 | 2/2013 | Lange et al. |
| 2013/0053892 | A1 | 2/2013 | Hawkins et al. |
| 2013/0065698 | A1 | 3/2013 | Biedermann et al. |
| 2013/0090693 | A1 | 4/2013 | Strausbaugh et al. |
| 2013/0096618 | A1 | 4/2013 | Chandanson et al. |
| 2013/0096622 | A1 | 4/2013 | Biedermann et al. |
| 2013/0103098 | A1 | 4/2013 | Jackson et al. |
| 2013/0110176 | A1 | 5/2013 | Rezach et al. |
| 2013/0110178 | A1 | 5/2013 | Biedermann et al. |
| 2013/0123858 | A1 | 5/2013 | Attia |
| 2013/0138161 | A1 | 5/2013 | Jackson |
| 2013/0165977 | A1 | 6/2013 | Biedermann et al. |
| 2013/0197583 | A1 | 8/2013 | Arnold et al. |
| 2013/0218207 | A1* | 8/2013 | Carls .............. A61B 17/7035 |
| | | | 606/278 |
| 2013/0226243 | A1 | 8/2013 | Kraus |
| 2013/0253596 | A1 | 9/2013 | Crook et al. |
| 2013/0274817 | A9 | 10/2013 | Jackson |
| 2013/0289632 | A1 | 10/2013 | Jackson |
| 2013/0338721 | A1 | 12/2013 | Biedermann et al. |
| 2014/0012275 | A1 | 1/2014 | Jackson |
| 2014/0012319 | A1 | 1/2014 | Jackson |
| 2014/0012331 | A1 | 1/2014 | Jackson |
| 2014/0012332 | A1 | 1/2014 | Jackson |
| 2014/0018863 | A1 | 1/2014 | Jackson et al. |
| 2014/0018864 | A1 | 1/2014 | Jackson |
| 2014/0025119 | A1 | 1/2014 | Biedermann et al. |
| 2014/0025120 | A1 | 1/2014 | Farris |
| 2014/0094849 | A1 | 4/2014 | Spratt et al. |
| 2014/0142634 | A1 | 5/2014 | Schlaepfer et al. |
| 2014/0142635 | A1 | 5/2014 | Purcell et al. |
| 2014/0200617 | A1 | 7/2014 | Farris et al. |
| 2014/0214084 | A1 | 7/2014 | Jackson et al. |
| 2014/0228887 | A1 | 8/2014 | Raju et al. |
| 2014/0228889 | A1 | 8/2014 | Shluzas |
| 2014/0228890 | A1 | 8/2014 | Raju et al. |
| 2014/0249582 | A1 | 9/2014 | Strausbaugh et al. |
| 2014/0277152 | A1 | 9/2014 | Hammer et al. |
| 2014/0277153 | A1 | 9/2014 | Spratt et al. |
| 2014/0277158 | A1 | 9/2014 | Spratt et al. |
| 2014/0277159 | A1 | 9/2014 | Spratt et al. |
| 2014/0277161 | A1 | 9/2014 | Spratt et al. |
| 2014/0296920 | A1 | 10/2014 | Biedermann et al. |
| 2014/0343617 | A1 | 11/2014 | Hannen |
| 2014/0358182 | A1 | 12/2014 | Puekert |
| 2015/0012046 | A1 | 1/2015 | Saint-Martin |
| 2015/0025579 | A1 | 1/2015 | Biedermann et al. |
| 2015/0032160 | A1 | 1/2015 | Carbone et al. |
| 2015/0032162 | A1 | 1/2015 | Biedermann et al. |
| 2015/0080960 | A1 | 3/2015 | Biedermann et al. |
| 2015/0088202 | A1 | 3/2015 | Charvet |
| 2015/0088207 | A1 | 3/2015 | Arnold et al. |
| 2015/0094776 | A1 | 4/2015 | Biedermann et al. |

(56) References Cited

U.S. PATENT DOCUMENTS

| | | |
|---|---|---|
| 2015/0105827 A1 | 4/2015 | Martin et al. |
| 2015/0119942 A1 | 4/2015 | Jackson et al. |
| 2015/0134004 A1 | 5/2015 | Ziolo et al. |
| 2015/0134006 A1 | 5/2015 | Ziolo et al. |
| 2015/0142059 A1 | 5/2015 | Biedermann et al. |
| 2015/0142061 A1 | 5/2015 | Courtney et al. |
| 2015/0148845 A1 | 5/2015 | Landry et al. |
| 2015/0148848 A1 | 5/2015 | Doubler et al. |
| 2015/0157365 A1 | 6/2015 | McKinley et al. |
| 2015/0182261 A1 | 7/2015 | Lovell et al. |
| 2015/0190176 A1 | 7/2015 | Jackson et al. |
| 2015/0196329 A1 | 7/2015 | Biedermann et al. |
| 2015/0196337 A1 | 7/2015 | Biedermann et al. |
| 2015/0196338 A1 | 7/2015 | Biedermann et al. |
| 2015/0201972 A1 | 7/2015 | Doubler et al. |
| 2015/0230829 A1 | 8/2015 | Harris et al. |
| 2015/0272626 A1 | 10/2015 | Spratt et al. |
| 2015/0282843 A1 | 10/2015 | Spitler |
| 2015/0282844 A1 | 10/2015 | Vedula et al. |
| 2015/0305781 A1 | 10/2015 | Landry et al. |
| 2015/0320465 A1 | 11/2015 | Butler et al. |
| 2015/0327888 A1 | 11/2015 | Shluzas |
| 2016/0000471 A1 | 1/2016 | Konieczynski et al. |
| 2016/0015429 A1 | 1/2016 | Butler |
| 2016/0030090 A1 | 2/2016 | Webb |
| 2016/0045228 A1 | 2/2016 | Biedermann et al. |
| 2016/0066961 A1 | 3/2016 | Biedermann et al. |
| 2016/0120578 A1 | 5/2016 | Farris |
| 2016/0128733 A1 | 5/2016 | Spratt et al. |
| 2016/0135848 A1 | 5/2016 | Chandanson et al. |
| 2016/0143678 A1 | 5/2016 | Biedermann et al. |
| 2016/0157895 A1 | 6/2016 | Hestad et al. |
| 2016/0183982 A1 | 6/2016 | Bazille |
| 2016/0192965 A1 | 7/2016 | Biedermann et al. |
| 2016/0206357 A1 | 7/2016 | Whipple |
| 2016/0220281 A1 | 8/2016 | Biedermann et al. |
| 2016/0228169 A9 | 8/2016 | Jackson |
| 2016/0296256 A1 | 10/2016 | Chandanson et al. |
| 2017/0020576 A1 | 1/2017 | Siccardi et al. |
| 2017/0049482 A1 | 2/2017 | Campbell et al. |
| 2017/0281241 A1 | 10/2017 | Jackson et al. |
| 2017/0311988 A1 | 11/2017 | Petit |
| 2018/0263662 A1 | 9/2018 | Lin et al. |
| 2018/0325569 A1 | 11/2018 | Ramsay et al. |

FOREIGN PATENT DOCUMENTS

| | | |
|---|---|---|
| WO | 2005018471 A1 | 3/2005 |
| WO | 2010111470 A1 | 9/2010 |
| WO | 2011047251 A1 | 4/2011 |

* cited by examiner

POLYAXIAL BONE SCREW WITH INCREASED ANGULATION

CROSS-REFERENCE TO RELATED APPLICATIONS

This application is a continuation of U.S. application Ser. No. 15/664,398, filed on Jul. 31, 2017, the disclosure of which is incorporated herein by reference.

TECHNICAL FIELD

The present disclosure relates generally to spinal surgery, and more particularly to polyaxial bone screws with increased angulation.

BACKGROUND OF THE INVENTION

The spinal column is a complex system of bones and connective tissues that provide support for the human body and protection for the spinal cord and nerves. The adult spine is comprised of an upper and lower portion. The upper portion contains 24 discrete bones, which are subdivided into three areas including 7 cervical vertebrae, 12 thoracic vertebrae and 5 lumbar vertebrae. The lower portion is comprised of the sacral and coccygeal bones. The cylindrical shaped bones, called vertebrae or vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The pedicle connects the lamina to the vertebral body.

The spine is a flexible structure capable of a large range of motion. There are various disorders, diseases, and types of injury which restrict the range of motion of the spine or interfere with important elements of the nervous system. The problems include, but are not limited to scoliosis, kyphosis, excessive lordosis, spondylolisthesis, slipped or ruptured discs, degenerative disc disease, vertebral body fracture, and tumors. Persons suffering from any of the above conditions may experience extreme or debilitating pain and diminished nerve function. These conditions and their treatments can be further complicated if the patient is suffering from osteoporosis, or bone tissue thinning and loss of bone density. Spinal fixation apparatuses are widely employed in surgical procedures for correcting spinal injuries and diseases. When the disc has degenerated to the point of requiring removal, there are a variety of interbody implants that are utilized to take the place of the disc. These include polyetheretherketone ("PEEK") interbody spacers, metal cages, and cadaver and human bone implants. In order to facilitate stabilizing the spine and keeping the interbody in position, other implants are commonly employed, including longitudinally linked rods secured to coupling elements, which in turn are secured to the bone by spinal bone fixation fasteners such as pedicle screws utilized to facilitate stabilization of bone.

BRIEF SUMMARY OF THE INVENTION

In general, the present disclosure is directed to a polyaxial bone screw device including a screw and a screw housing. The screw housing defines a longitudinal axis and a notch configured to receive a portion of the screw. The notch is configured to enable increased angulation of the screw relative to the longitudinal axis of the screw housing in response to relative pivotal movement between the screw and screw housing. The polyaxial bone screw device may include a spring that is positioned to frictionally engage the screw to maintain the screw in an angled position relative to the screw housing.

In accordance with an aspect of the present disclosure, a polyaxial bone screw device includes a screw, a screw housing, and a spring. The screw includes a screw head and a shaft that extends from the screw head. The screw housing defines a longitudinal axis and a bore that extends along the longitudinal axis. The screw housing includes a basewall and opposed sidewalls that extend from the basewall. The basewall defines a notch configured to receive a portion of the shaft therein. The notch is configured to selectively increase pivotal movement between the screw and the screw housing relative to the longitudinal axis of the screw housing in the direction of the notch. The opposed sidewalls define a rod-receiving channel. The screw housing further defines a transverse hole that is in communication with the bore. The spring is supported in the transverse hole of the screw housing and extends therethrough. The spring extends into the bore of the screw housing to frictionally engage the screw head of the screw while the screw head is seated in the bore of the screw housing.

In disclosed embodiments, the spring may be configured to maintain the shaft at an angular position relative to the longitudinal axis of the screw housing while frictionally engaged with the screw head.

In certain embodiments, the screw head may include an outer surface that is configured to facilitate frictional engagement with the spring.

In some embodiments, the polyaxial bone screw device may further include an anvil disposed within the screw housing and positioned to support a spinal rod seated within the rod-receiving channel. The anvil may be seated on the screw head while a portion of the anvil is configured to engage the spring. The spring may be frictionally engaged with the screw head while engaged to the portion of the anvil to support the screw in a position relative to the screw housing.

In disclosed embodiments, the screw housing may be pivotable in a first direction relative to the screw to a first angle and may be pivotable in a second direction relative to the screw to a second angle. The first angle may be different than the second angle. The shaft of the screw may be positioned within the notch of the screw housing while disposed in the first angle.

In certain embodiments, the first angle is about 60 degrees relative to the longitudinal axis of the screw housing and the second angle is about 45 degrees relative to the longitudinal axis of the screw housing.

In disclosed embodiments, the polyaxial bone screw device may further include a pin disposed within the transverse hole to support the spring therein.

In some embodiments, the polyaxial bone screw device may further include a set screw configured to be threadably received within the screw housing to secure a spinal rod within the screw housing.

According to another aspect of the present disclosure, a method of securing a spinal rod to a polyaxial bone screw is provided. The method includes inserting a polyaxial bone screw into bone. The polyaxial bone screw has a screw, a screw housing, and a spring. The screw has a head and a shaft extending therefrom. The shaft is insertable into bone. The screw housing includes opposed sidewalls that define a U-shaped rod-receiving channel. The screw housing further defines an opening for receiving the head of the screw, a notch for receiving a portion of the shaft, and a transverse hole. The spring extends through the transverse hole and is maintained by a pin disposed within the transverse hole.

The method includes positioning the screw housing relative to the screw. The screw housing is movable in a first direction relative to the screw to a first angle. The screw housing is movable in a second direction relative to the screw to a second angle. The first angle is greater than the second angle when the portion of the shaft of the screw is received in the notch of the screw housing at the first angle when the screw housing is moved in the first direction. The method further includes supporting the portion of the shaft in one or both of the first and second angles through frictional engagement between the spring and the head of the screw. The method includes coupling a spinal rod to the polyaxial bone screw by inserting a portion of the spinal rod into the U-shaped rod-receiving channel of the screw housing of the polyaxial bone screw.

The method may further include selectively pivoting the screw along a longitudinal axis of the spinal rod in the first direction relative to the screw housing to the first angle. Positioning the screw housing may include positioning the portion of the shaft within the notch such that the first angle is about 60 degrees relative to the longitudinal axis of the screw housing.

The method may further include selectively pivoting the screw along a longitudinal axis of the spinal rod in the second direction relative to the screw housing to the second angle. Positioning the screw housing may include positioning the portion of the shaft within another region of the screw housing that is separate from the notch such that the second angle is about 45 degrees relative to the longitudinal axis of the screw housing.

The method may include securing the spinal rod to the polyaxial bone screw by attaching a set screw to the screw housing.

BRIEF DESCRIPTION OF THE DRAWINGS

The accompanying drawings, which are incorporated in and constitute part of this specification, illustrate embodiments of the disclosure and, together with a general description of the disclosure given above, and the detailed description of the embodiments given below, serve to explain the principles of the disclosure, wherein.

DETAILED DESCRIPTION

Embodiments of the present disclosure are now described in detail with reference to the drawings in which like reference numerals designate identical or corresponding elements in each of the several views. As commonly known, the term "clinician" refers to a doctor, a nurse, or any other care provider and may include support personnel. Throughout the description, the term "proximal" refers to a portion of structure (e.g., a device or component thereof) closer to the clinician, while the term "distal" refers to a portion of structure farther from the clinician. Additionally, in the drawings and in the description that follows, terms such as "top," "bottom," "front", "back," "side," and similar directional terms are used simply for convenience of description and are not intended to limit the disclosure.

In the following description, well-known functions or constructions are not described in detail to avoid obscuring the present disclosure in unnecessary detail.

Figure 1:
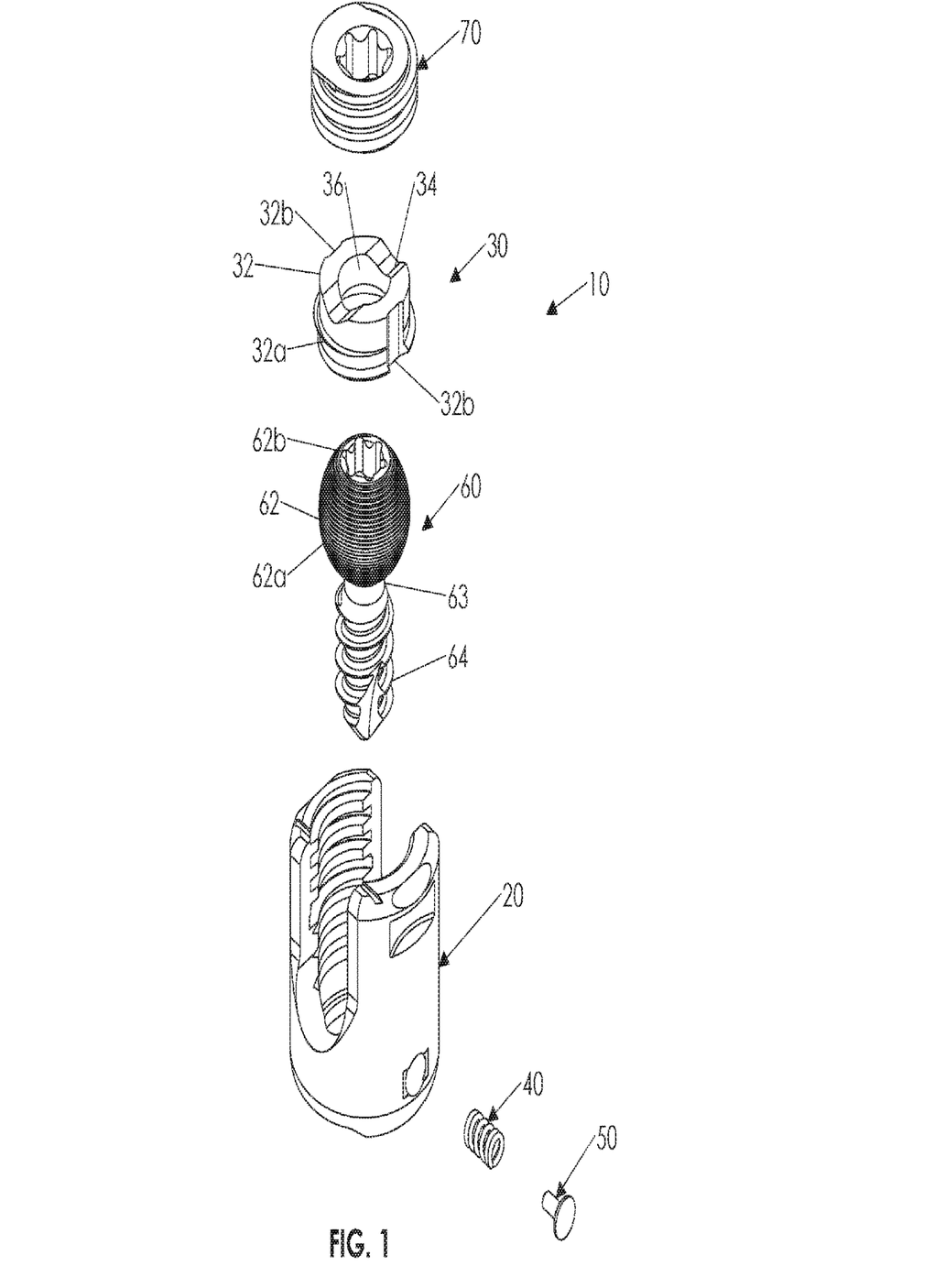
FIG. 1 is an exploded view, with parts separated, of a polyaxial bone screw in accordance with the present disclosure.
Figure 2A:
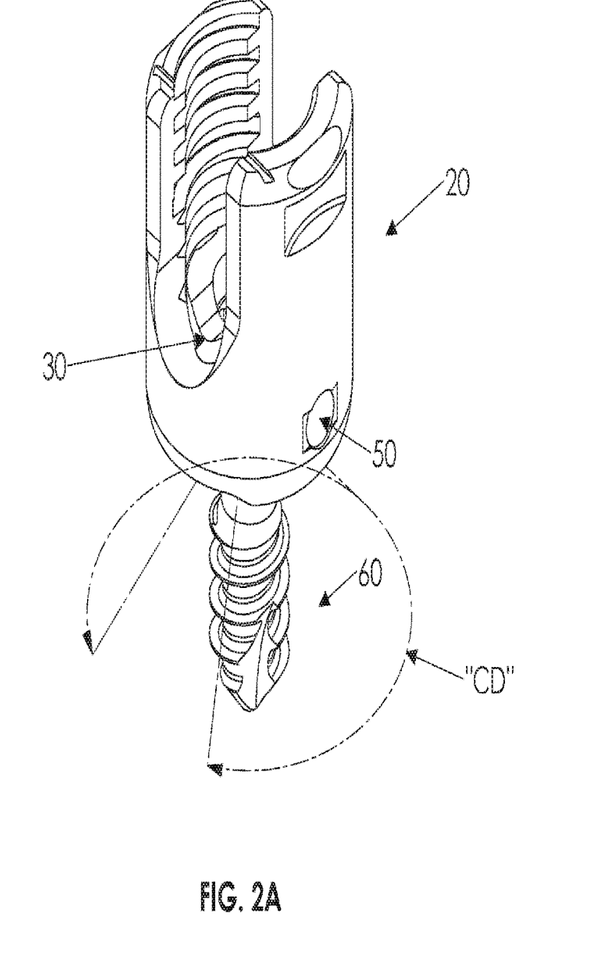
FIG. 2A is a perspective view of the polyaxial bone screw of FIG. 1 with a set screw thereof removed for clarity.
Figure 2B:
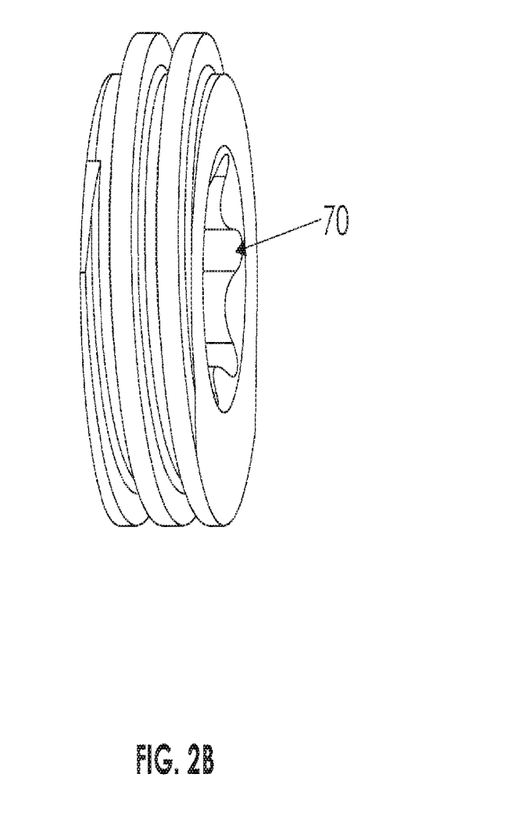
FIG. 2B is a side, perspective view of the set screw of the polyaxial bone screw of FIG. 1.
Figure 6A:
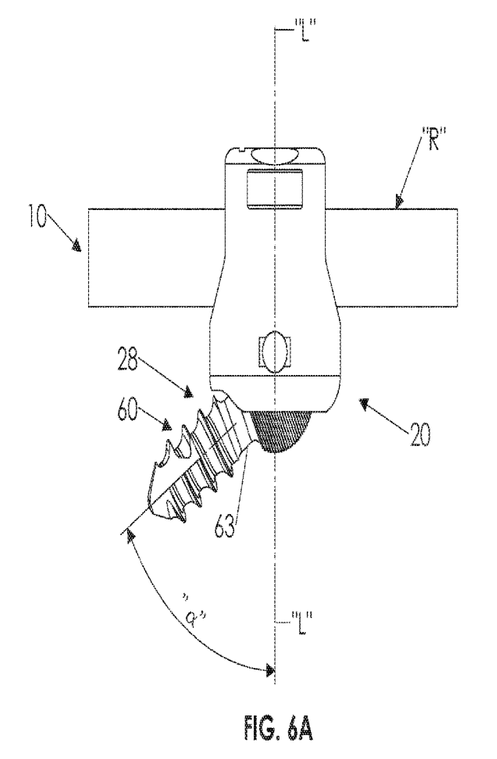
FIG. 6A is a side view of the polyaxial bone screw of FIG. 2A shown coupled to a spinal rod with the screw shaft depicted at a first angle relative to the screw housing.
Figure 6B:
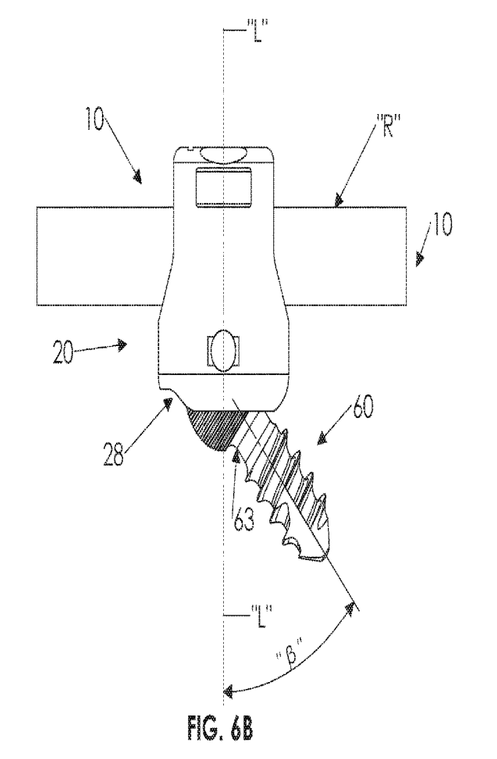
FIG. 6B is a side view of the polyaxial bone screw of FIG. 2A with the polyaxial bone screw depicted at a second angle relative to the screw housing.

With reference to FIGS. 1, 2A and 2B, a polyaxial bone screw 10 generally includes a screw housing 20, an anvil 30, a spring 40 (e.g., a compression spring), a pin 50, a screw 60, and a set screw 70. The polyaxial bone screw 10 is configured to be cooperatively engaged to a spinal rod "R" (FIGS. 6A and 6B).

With reference to FIGS. 3-5A, the screw housing 20 of the polyaxial bone screw 10 defines a longitudinal axis "L" and has a generally cylindrical shape. The screw housing 20 extends from a proximal end 20a defining a proximal opening 21a to a distal end 20b defining a distal opening 21b. The proximal and distal ends 20a and 20b, respectively, of the screw housing 20 may be disposed in parallel relation. The screw housing 20 further includes opposing first and second sidewalls 20c, 20d that extend proximally from the distal end 20b of the basewall 20f of the screw housing 20 and define a generally U-shaped rod-receiving channel 22 therebetween. Each of the first and second sidewalls 20c, 20d defines an external flanged recess 23 that is configured to facilitate grasping of the screw housing 20 by an instrument (not shown) that can also be used to facilitate insertion of the polyaxial bone screw 10 into a vertebral body.

The annular basewall 20f of the screw housing 20 extends distally to the distal end 20b of the screw housing 20. The screw housing 20 defines a threaded internal surface 20e and a rod slot or rod-receiving channel 22 through a proximal portion of the screw housing 20, and a central bore 24 through the screw housing 20 from the proximal opening 21a defined in the proximal end 20a of the screw housing 20 to the distal opening 21b defined in the distal end 20b of the screw housing 20. The rod-receiving channel 22 is configured to receive a spinal rod "R" (FIGS. 6A and 6B) therein and the threaded internal surface 20e is configured to threadably receive a set screw 70 (FIG. 2B) for securing the spinal rod "R" in the screw housing 20. The annular basewall 20*f* of the screw housing 20 includes a central portion 20*g* aligned with the rod-receiving channel 22 and first and second side portions 20*h*, 20*i* aligned with the first and second sidewalls 20*c*, 20*d*, respectively. The first side portion 20*h* of the annular basewall 20*f* defines a transverse hole 26 that receives the spring 40 and pin 50. The transverse hole 26 is in communication with the bore 24 to enable the spring 40 to extend through the basewall 20*f* and into the bore 24. The central portion 20*g* of the annular basewall 20*f* includes a front wall 20*j* and a back wall 20*k*. The screw housing 20 defines a relief groove or notch 28 that may be milled out of the annular basewall 20*f*. Although shown as positioned on the front wall 20*j*, the notch 28 may be positioned at any suitable location along the basewall 20*f* (e.g., back wall 20*k*, first side portion 20*h*, second side portion 20*i*, etc.). In this regard, it will be appreciated that while the notch is shown disposed on front wall 20*j*, such that when the screw pivots in the direction of the notch it pivots parallel to a rod disposed in the rod slot, the notch may be disposed in one of side walls 20*h*, 20*i* such that when the screw pivots in the direction of the notch it pivots perpendicular to or at an angle with respect to the direction of the rod slot, or a rod disposed in the rod slot.

With reference to FIGS, the notch 28 is defined by a planar surface 28*a* connected to arcuate surfaces 28*b* (e.g., defined by a diameter ranging from about 0.092 inches to about 0.096 inches in certain embodiments) disposed on opposite ends of the planar surface 28*a*. Each of the arcuate surfaces 28*b* extends distally from the planar surface 28*a* to angled edges 28*c*. The angled edges 28*c*, which in certain embodiments, may be angled about 45 degrees relative to the longitudinal axis "L," extend to the distal end 20*b* of the screw housing 20. In certain embodiments, the diameter of the distal end 20*b* of the screw housing 20 may be about 0.275 inches. In certain embodiments, the height of the notch 28 relative to distal end 20*b* may range from about 0.034 inches to about 0.038 inches. Although the notch 28 is shown to extend along an arc angle of about 60 degrees (e.g., 30 degrees from centerline/midpoint thereof) around a circumference of the screw housing 20, the notch 28 may, in some embodiments, extend around a greater or lesser arc angle, e.g., up to about 180 degrees. In some embodiments, the arc angle may measure up to about 90 degrees. In embodiments, the arc angle may measure up to about 30 degrees. In general, dimensions of the notch 28 will depend upon the amount of angulation and/or dimensions of screw 60.

Figure 3:
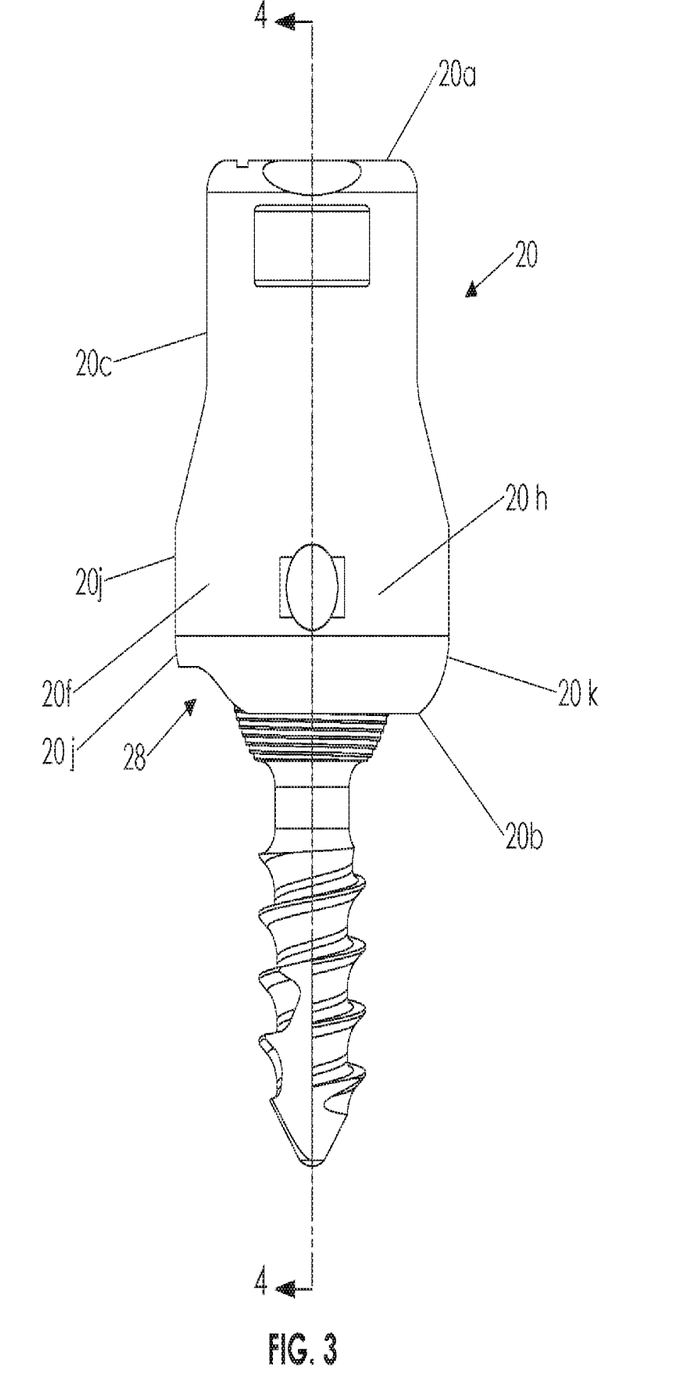
FIG. 3 is a side view of the polyaxial bone screw of FIG. 2A.
Figure 3A:
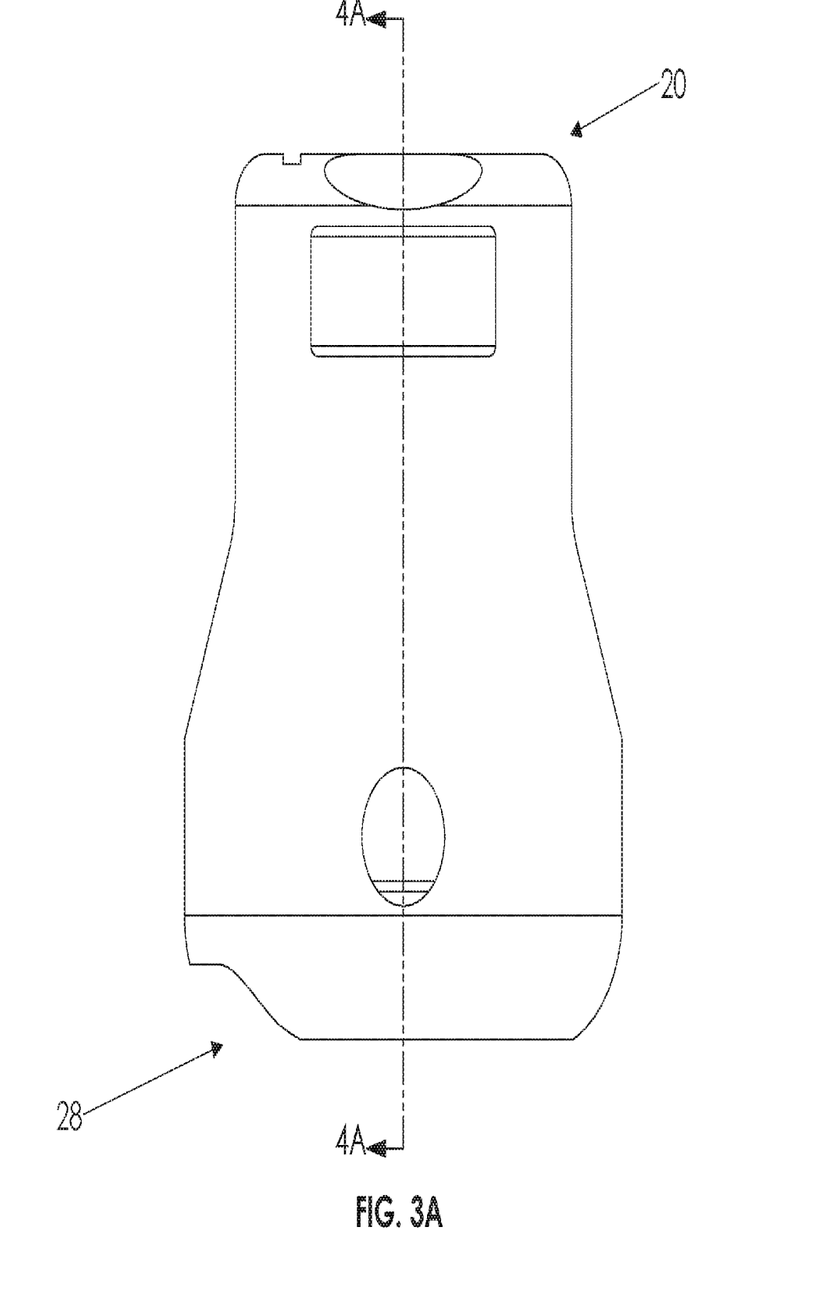
FIG. 3A is a side view of a screw housing of the polyaxial bone screw of FIG. 1.
Figure 3B:
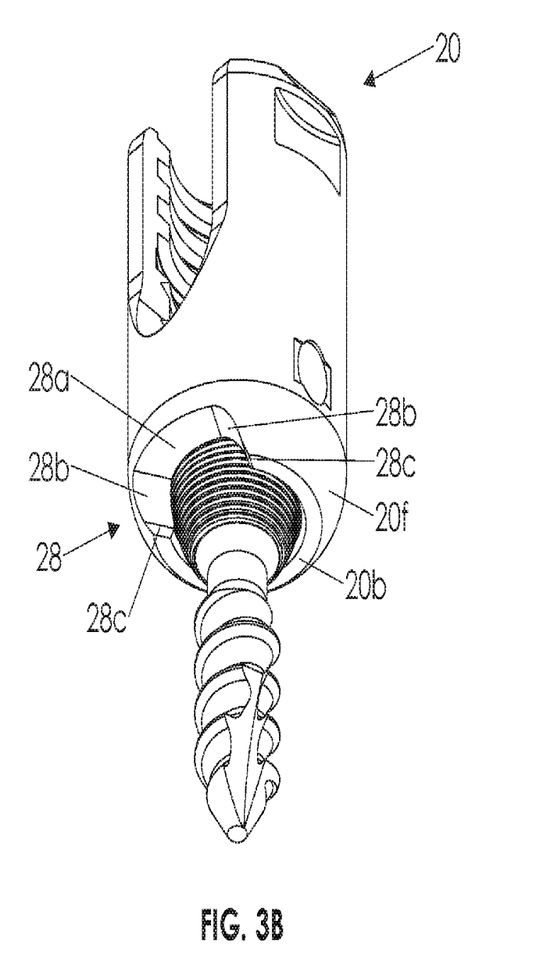
FIG. 3B is a bottom perspective view of the polyaxial bone screw of FIG. 3.

The centerline/midpoint of the notch 28 may be aligned with an axis of the U-shaped rod-receiving channel 22 (FIGS. 3A and 3B). In some embodiments, the centerline/midpoint of the notch 20 may be positioned such that the notch 28 is rotationally offset from the axis defined by the U-shaped rod-receiving channel 22.

As can be appreciated, one or more of the dimensions of the notch 28 disclosed herein may be provided to enable the polyaxial bone screw 10 to achieve an increased angulation of about 15 degrees (e.g., up to 60 degrees in a first pivot angle as compared to 45 degrees in a second pivot angle). The ratios of two or more of the disclosed dimensions may be predefined to enable such increased/optimized angulation (e.g., height of notch 28 to degree of angulation).

Figure 4:
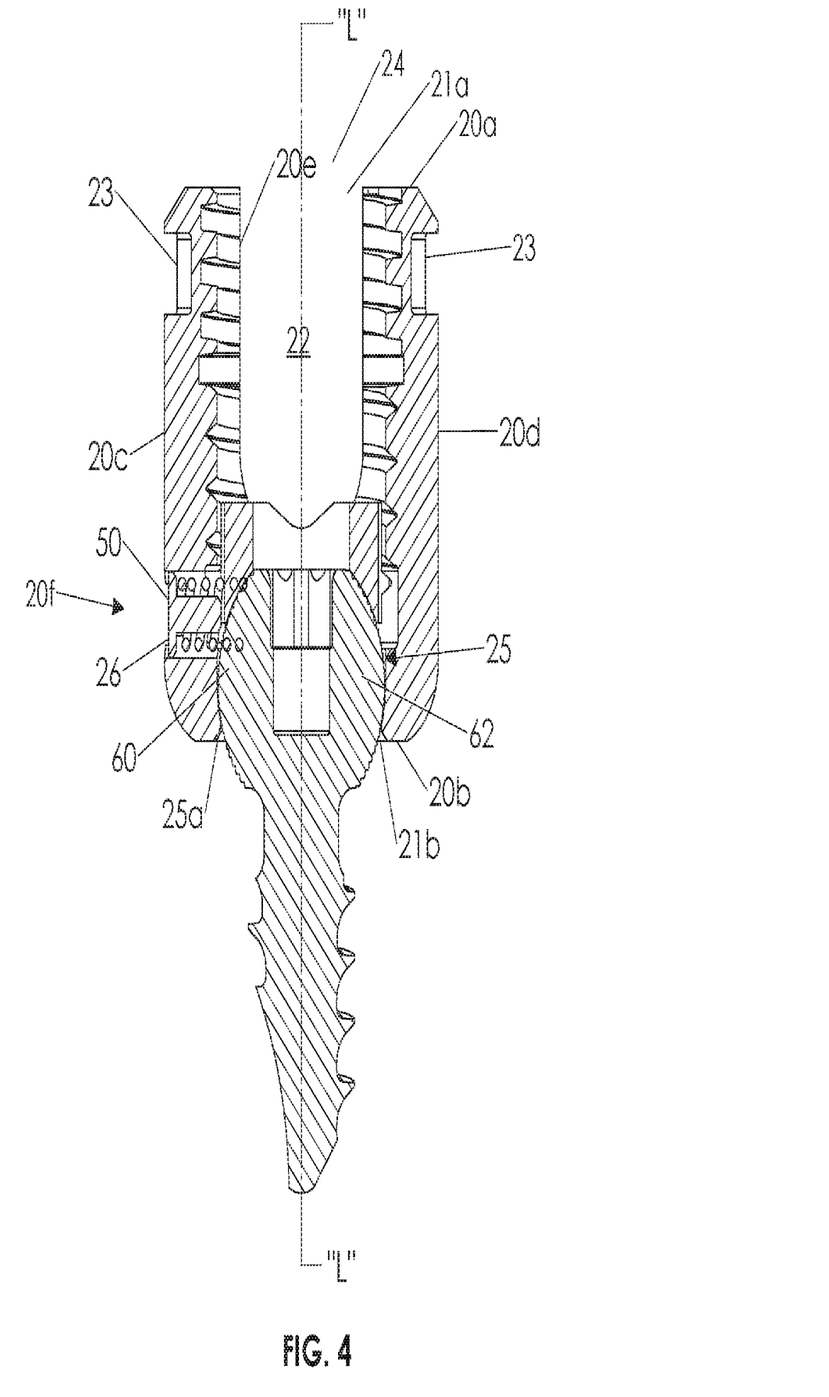
FIG. 4 is a cross-sectional view of the polyaxial bone screw of FIG. 3 taken along section line 4-4.
Figure 4A:
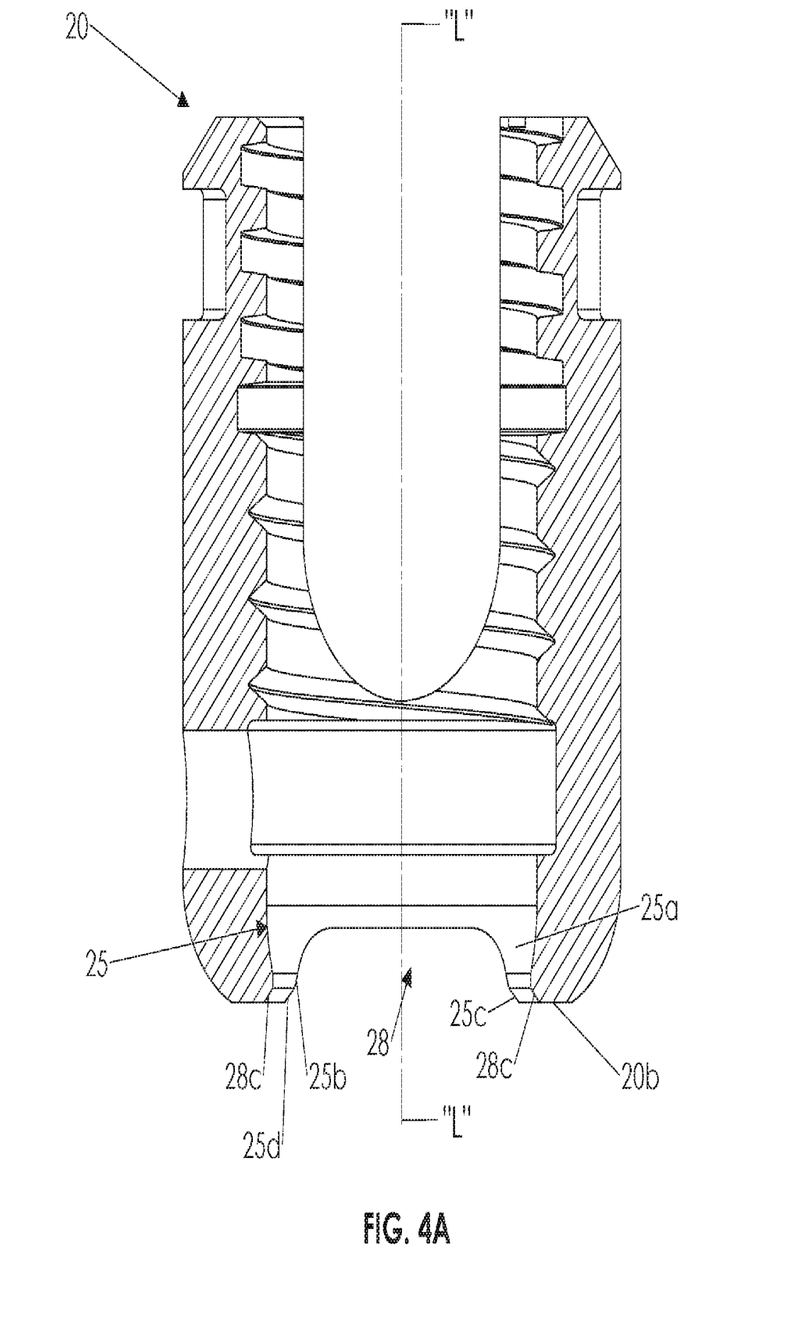
FIG. 4A is a cross-sectional view of the screw housing of FIG. 3A taken along section line 4A-4A.
Figures 5, 5A:
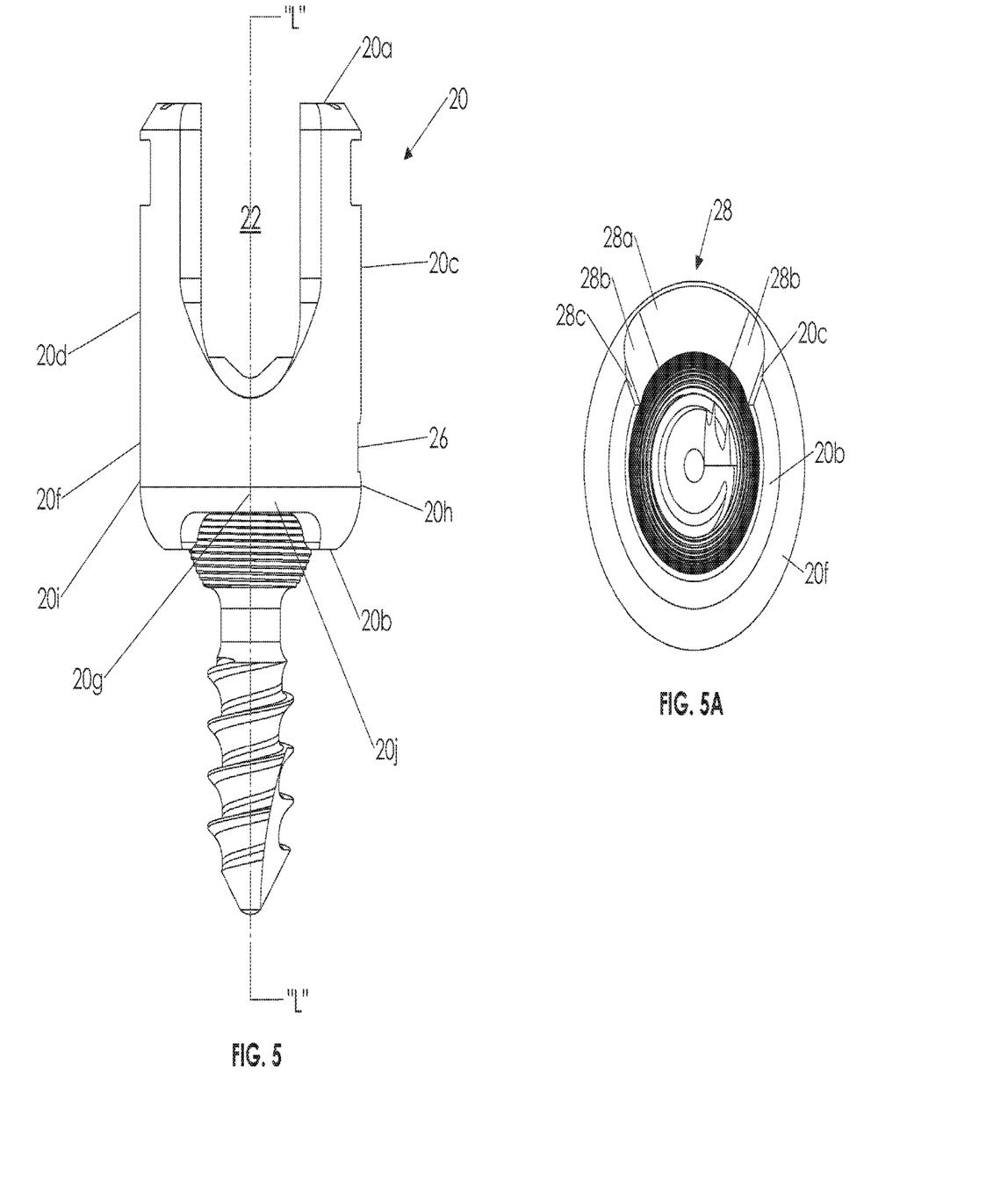
FIG. 5 is a front view of the polyaxial bone screw of FIG. 2A.
FIG. 5A is a bottom view of the polyaxial bone screw of FIG. 5.

Referring to FIGS. 4 and 4A, the annular basewall 20*f* of the screw housing 20 further includes an internal surface 25 that defines a seat 25*a* for supporting the head 62 of the screw member 60 at an internal location spaced-apart from, and proximal to, a distal end of the screw housing 20. The seat 25*a* extends to an inner edge 25*b*, which may be C-shaped, and which includes first and second ends 25*c*, 25*d* that circumferentially terminate at the notch 28. The inner edge 25*b* is disposed adjacent to the angled edges 28*c* of the notch 28 and the distal end 20*b* of the screw housing 20. In some embodiments, the seat 25*a* has a diameter ranging between about 0.219 inches to about 0.223 inches.

Referring again to FIGS. 1 and 4, the screw member 60 of the polyaxial bone screw 10 includes a head 62 (e.g., spherically-shaped) that is positioned in contact with the seat 25*a* of the screw housing 20 to support the screw member 60 in the screw housing 20, a neck 63 that extends distally from a distal end of the head 62 to a threaded shaft 64. The threaded shaft 64 extends distally from a distal end of the neck 63 to a distal end of the screw member 60. The head 62 includes a textured or uneven outer surface 62*a* (e.g., annular ribs, ridges, etc.) that is configured to frictionally engage with the spring 40 while the spring 40 is engaged with the anvil 30 to maintain the screw member 60 in position relative to the screw housing 20. The head 62 defines a driving recess 62*b* (e.g., hexolobular or the like) defined in a proximal end thereof for receiving a driving tool (e.g., screw driver) (not shown) configured to screw the threaded shaft 64 of the screw member 60 into a hole in bone as the driving tool rotates the head 62 of the screw member 60. In particular, the screw member 60, while assembled to the screw housing 20, is configured to be screwed to a vertebral body such as the lateral mass of the "atlas" vertebra (the "atlas" vertebra is anatomical parlance for the commonly designated C1 vertebra—not shown).

With continued reference to FIGS. 1 and 4, the anvil 30 of the polyaxial bone screw 10 is threaded into the screw housing 20 and positioned on the head 62 of the screw member 60 and in locking engagement with the spring 40. The anvil 30 includes an annular anvil body 32, which may be cylindrically-shaped, and defines a saddle 34 configured to support the spinal rod "R" (FIG. 6). The saddle 34 may be U-shaped. The annular anvil body 32 includes a threaded outer surface 32*a* that is threadably engaged with the threaded internal surface 20*e* of the screw housing 20 and positioned atop the head 62 of the screw member 60. The threaded outer surface 32*a* further includes a pair of side slots 32*b* extending axially along the threaded outer surface 32 on opposed sides of the threaded outer surface 32*a*. One of the slots 32*b* receives the spring 40 to enable the spring 40 to rotatably lock the anvil 30 in position relative to the screw housing 20 such that the rod-receiving channel 22 of the screw housing 20 and the saddle 34 of the anvil 30 are aligned. The annular anvil body 32 defines a central opening 36 therethrough to provide screw-driving access to the drive recess 62*b* of the screw member 60.

Figure 7:
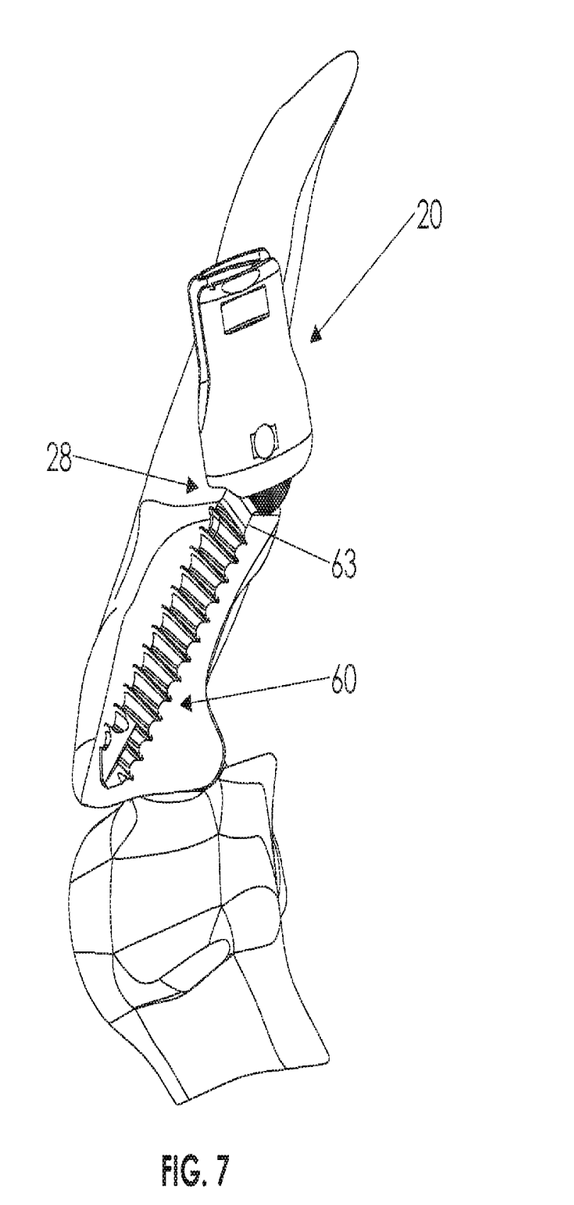
FIG. 7 is a perspective view of the polyaxial bone screw of FIG. 2A inserted into bone.
Figure 8:
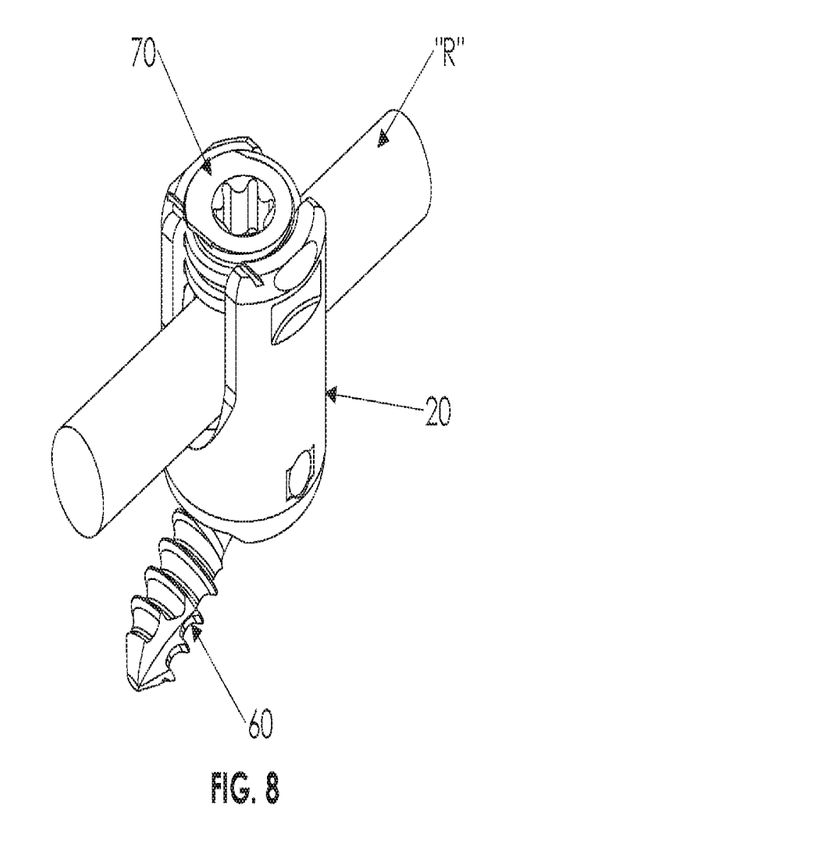
FIG. 8 is a perspective view of the polyaxial bone screw of FIG. 6A.

As seen in FIGS. 6-8, the screw housing 20 is configured to be polyaxially movable (e.g., pivotable and rotatable) relative to the screw member 60, for example, to accommodate the spinal rod "R" at various angular and/or rotational orientations. For instance, the screw housing 20 is movable in a first direction relative to the screw member 60 to receive the neck 63 of the screw member 60 within the notch 28. With the neck 63 positioned within the notch 28, the screw member 60 is pivoted away from the longitudinal axis "L" of the screw housing 20 to define a first pivot angle "α" relative to the longitudinal axis "L". Although the first pivot angle "α" is shown to measure about 60 degrees, in certain embodiments, the first pivot angle "α" may range between 50 degrees to about 70 degrees, or more preferably between about 55 degrees to about 65 degrees. In some embodiments, the first pivot angle "α" may range between 45 degrees to about 90 degrees.

The screw housing 20 is also movable in conical directions "CD" (FIG. 2A) relative to the screw member 60 that do not position the screw member 60 in registration with the notch 28 when the screw member 60 is pivoted away from the longitudinal axis "L." These conical directions "CD" include medial-lateral directions (e.g., directions transverse to the spinal rod "R") and (e.g., cranial-caudally and in-plane with spinal rod "R"—FIG. 7), at a second pivot angle "β". For instance, the screw housing 20 is movable in a second direction (e.g., conical directions) relative to the screw member 60 to engage the neck 63 of the screw member 60 at the distal end 20b of the screw housing 20. With the neck 63 engaged with the distal end 20b, the screw member 60 is pivoted away from the longitudinal axis "L" of the screw housing 20 to define a second pivot angle "β" relative to the longitudinal axis "L". Although the second pivot angle "β" is shown to measure about 45 degrees, in certain embodiments, the second pivot angle "β" may range between about 40 degrees to about 50 degrees. In some embodiments, the second pivot angle "β" may range between about 35 degrees to about 55 degrees.

In this arrangement, the notch 28 is configured to provide about ⅓ more angulation between the screw member 60 and the screw housing 20 in the first pivot angle "α" as compared to the second pivot angle "β". Such arrangement helps to optimize angulation while maintaining structural integrity/strength of screw housing 20.

Manufacturing of the polyaxial bone screw 10 may involve machining the screw housing 20, the anvil 30, the pin 50, the screw member 60, and the set screw 70 in a lathe or screw machine. The notch 28 of the screw housing 20 may be notched out of the screw housing 20 in a separate milling operation. The spring 40 may be separately coiled.

In assembling the polyaxial bone screw 10, the threaded shaft 64 of the screw member 60 is passed through the screw housing 20 until the head 62 of the screw member 60 is rests on the seat 25a of the screw housing 20. Next, the threaded outer surface 32a of the anvil 30 is threaded along the threaded internal surface 20e of the screw housing 20 until it seats onto the head 62 of the screw member 60 with the U-shaped saddle 34 of the anvil 30 aligned with the rod-receiving channel 22 of the screw housing 20. The pin 50 and the spring 40 are then inserted into the transverse hole 26 of the screw housing 20. A staking tool (not shown) may then utilized to deform the edges of the transverse hole 26 of the screw housing 20 to fixedly retain the pin 50 and the spring 40 in the transverse hole 26 such that the spring 40 is disposed in frictional engagement with one of the side slots 32b of the anvil 30 and with the head 62 of the screw member 60.

In use, once the screw member 60 of the polyaxial bone screw 10 is screwed into bone (e.g., vertebral body) the screw housing 20 of the polyaxial bone screw 10 can be movable relative to the screw member 60 through any of the angles detailed above to enable the screw housing 20 to receive the spinal rod "R" in the rod-receiving channel 22 of the screw housing 20. The frictional engagement between the head 62 of the screw member 60 and the spring 40 helps maintain the screw member 60 and the screw housing 20 at a desired angular orientation with respect to one another. Once the spinal rod "R" is supported in the screw housing 20 on the anvil 30, the spinal rod "R" can be secured to the polyaxial bone screw 10 by threading the set screw 70 into the screw housing 20 against the spinal rod "R," as seen in FIG. 8. Before fully tightening the set screw 70, the screw housing 20 and the spinal rod "R" therein can be further manipulated and/or pivoted relative to the screw member 60 to achieve a desired angular position of the spinal rod "R." Once the desired angular position of the spinal rod "R" is achieved, the set screw 70 can be fully tightened to fix the angular relationship between the screw housing 20 and the screw member 60 of the polyaxial bone screw 10.

The polyaxial bone screw system 10, or components thereof, may be formed from any suitable biocompatible material, including, for example, metals (e.g., a stainless steel, cobalt, chrome, titanium, and titanium alloy), polymers (e.g., PEEK, polyphenylsulfone, polyetherimide, polycarbonate, polyethylene, polypropylene, polyacetal, or other such engineering resin), or combinations of the aforementioned materials.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A polyaxial bone screw device, comprising:
a screw having a head and a shaft;
a screw housing defining a bore that extends along a longitudinal axis, the screw housing including:
   a basewall defining an aperture to receive a portion of the screw;
   opposed sidewalls that extend from the basewall and define a rod-receiving channel; and
   a transverse hole extending at least partially through one of the opposed sidewalls and being in communication with the bore;
an anvil disposed within the screw housing, the anvil having a body including a threaded surface for threadably mating the anvil within the screw housing and preventing the anvil from moving in a proximal direction upon application of a proximal force, the body of the anvil defining a saddle shaped surface for receiving a spinal rod seated within the rod-receiving channel; and
a spring disposed in the transverse hole of the screw housing, extending into the bore of the screw housing and applying a friction force to the screw head when the screw head is seated against the basewall of the screw housing.

2. The polyaxial bone screw device of claim 1, wherein the basewall further defines a notch configured to receive a portion of the screw.

3. The polyaxial bone screw device of claim 2, wherein when the screw is positioned along the longitudinal axis, the screw is pivotable in a first direction relative to the screw housing at a first angle and receivable within the notch, and pivotable in a second direction relative to the screw housing at a second angle different than the first angle.

4. The polyaxial bone screw device of claim 3, wherein the first angle is between approximately 50 degrees and 70 degrees relative to the longitudinal axis of the screw housing and the second angle is between approximately 35 degrees and 55 degrees relative to the longitudinal axis of the screw housing.

5. The polyaxial bone screw device of claim 4, wherein the first angle is about 60 degrees and the second angle is about 45 degrees.

6. The polyaxial bone screw device of claim 1, wherein the spring directly engages the screw head and is configured to maintain the shaft at an angular position relative to the longitudinal axis of the screw housing.

7. The polyaxial bone screw device of claim 1, wherein the screw head includes a textured outer surface that is configured to facilitate frictional engagement with the spring.

8. The polyaxial bone screw device of claim 7, wherein the textured outer surface comprises an annular rib or a ridge.

9. The polyaxial bone screw device of claim 1, wherein the anvil is seated on the screw head and the spring directly engages the anvil.

10. The polyaxial bone screw device of claim 1, wherein the spring directly engages both the anvil and the head of the screw and maintains the shaft of the screw at an angular position relative to the longitudinal axis of the screw housing.

11. The polyaxial bone screw device of 1, wherein the threaded surface defines a first axial slot.

12. The polyaxial bone screw device of claim 11, wherein the threaded surface further defines a second axial slot circumferentially spaced about the body of the anvil from the first axial slot.

13. The polyaxial bone screw device of claim 11, wherein the spring extends into the first axial slot.

14. The polyaxial bone screw device of claim 1, further comprising a pin disposed within the transverse hole and extending at least partially through the spring.

15. The polyaxial bone screw device of claim 1, further comprising a set screw threadably received within the bore of the screw housing to secure a spinal rod within the screw housing.

16. A method of assembling a polyaxial bone screw assembly, comprising:
providing a screw housing including a basewall and opposed sidewalls that extend from the basewall and collectively define a bore and a rod-receiving channel, the basewall defining a notch configured to receive a portion of a screw therein, the screw housing further defining a transverse hole extending through one of the opposed sidewalls and being in communication with the bore;
inserting a spring through the transverse hole of the screw housing, from an exterior of the sidewall into the bore of the screw housing, such that the spring is arranged to provide a friction force to a screw head when the screw is inserted into the bore of the screw housing.

17. The method of claim 16, further comprising:
inserting a pin into the transverse hole of the screw housing to support the spring.

18. The method of claim 16, further comprising:
inserting the screw into the bore of the screw housing;
inserting an anvil into the bore of the screw housing and into engagement with the head of the screw, the anvil having a body defining a slot;
positioning a portion of the spring into the axial slot; and
positioning a portion of the spring into direct engagement with the head of the screw.

* * * * *